United States Patent [19]

Richards et al.

[11] Patent Number: 4,847,193
[45] Date of Patent: Jul. 11, 1989

[54] SIGNAL AMPLIFICATION IN AN ASSAY EMPLOYING A PIEZOELECTRIC OSCILLATOR

[75] Inventors: James C. Richards, Framingham; David T. Bach, Westborough, both of Mass.

[73] Assignee: Gene-Trak Systems, Framingham, Mass.

[21] Appl. No.: 64,266

[22] Filed: Jun. 18, 1987

[51] Int. Cl.$^4$ ............................................. C12Q 1/68
[52] U.S. Cl. ........................................ 435/6; 436/501; 436/518; 436/524; 436/525; 436/528; 436/531; 436/806
[58] Field of Search ............... 436/528, 518, 524, 525, 436/526, 806, 501, 531; 435/6

[56] References Cited

U.S. PATENT DOCUMENTS

| | | |
|---|---|---|
| 4,236,893 | 12/1980 | Rice . |
| 4,242,096 | 12/1980 | Oliveira et al. ..................... 436/500 |
| 4,314,821 | 2/1982 | Rice . |
| 4,672,040 | 6/1987 | Josephson ......................... 436/526 |
| 4,735,906 | 4/1988 | Bastiaans ........................... 436/501 |

OTHER PUBLICATIONS

"Piezoelectric Sorption Detector", William H. King, Jr., vol. 26, No. 9, Aug. 1964, *Analytical Chemistry*.

"An Immunospecific Microbalance", Shons et al., *Journal of Biomedical Materials*, vol. 6, pp. 565–570 (1972).

"Attachment of Nucleic Acids to Piezoelectric Crystals for Detection of Hybridization by Change in Mass", Flowers et al., Chemistry of DNA and RNA (204–207).

*Primary Examiner*—Robert J. Warden
*Assistant Examiner*—Stephen C. Wieder

[57] ABSTRACT

A method for detecting a first member of a specific binding pair in a sample, the first member being capable of forming a complex with a second member of the specific binding pair, includes immobilizing the second member on a surface of a piezoelectric oscillator, determining a first vibrational frequency of the oscillator on which the second member has been immobilized, contacting the surface of the oscillator on which the second member has been immobilized with the sample under conditions permitting formation of the complex, and with a particle under conditions permitting binding of the particle with the first member, mass coupling the bound particle with the oscillator, and determining a second vibrational frequency of the oscillator with which the particle has been mass coupled, the difference between the first vibrational frequency and the second vibrational frequency providing a measure of the quantity of the first member in the sample.

20 Claims, No Drawings

SIGNAL AMPLIFICATION IN AN ASSAY EMPLOYING A PIEZOELECTRIC OSCILLATOR

BACKGROUND OF THE INVENTION

This invention relates to methods employing piezoelectric oscillators for detecting members of specific binding pairs.

A piezoelectric oscillator in common use as a frequency standard in electronic equipment typically consists of a quartz crystal, cut in a particular plane in the shape of a thin wafer and having a layer of metal deposited on each of the two larger parallel planar surfaces as electrodes.

When placed in an appropriate oscillator circuit, the crystal vibrates at or extremely near its natural or native frequency of vibration. It is well known that coupling a mass to the surfaces of such a piezoelectric oscillator causes a shift downward in the vibrational frequency of the oscillator, and that the amount of change in frequency is related to the amount of mass. This relationship between the mass coupled to the oscillator and the frequency shift forms the basis for using such an oscillator as a mass sensor, or so-called piezoelectric microbalance, as described in W. H. King, 1964, Anal. Chem., vol. 36(a), pages 1735-39.

A. Shons et al., *J. Biomed. Mater. Res.*, vol. 6, pages 565-70, describes using a piezoelectric microbalance to determine the quantity of a given antibody in a solution, by coating the crystal surface with an antigen specific for the antibody and measuring the vibrational frequency, then exposing the antigen-coated surface to the antibody in solution to allow formation of the specific antigen-antibody binding pairs, and then again measuring the vibrational frequency and computing the mass of bound antibody from the frequency shift.

T. K. Rice, 1980, U.S. Pat. No. 4,236,893, describes determining a particular class of antibody by exposing a surface of a piezoelectric oscillator, previously coated with an antigen specific to the antibody, to a test solution containing an unknown amount of the antibody, allowing the antibody to bind to the antigen, and then exposing the surface to a sandwiching substance which selectively binds to the specific subclass of the antibody being determined. The amount of the specific subclass bound on the oscillator (and thus in the test solution) is related to the shift in vibrational frequency resulting from the addition of the sandwiching substance. T. K. Rice, 1982, U.S. Pat. No. 4,314,821, describes determining the amount of an immunologically-reactive substance in a liquid test solution containing interfering material that can bind to an antigen by contacting a surface of a piezoelectric oscillator, previously coated with an antigen specific to the antibody, to the test solution, allowing any of the antibody that may be present in the test solution to bind with the antigen, and then exposing the surface to an excess of a substance specifically reactive with all of the bound antibody and not with the interfering material. The amount of the antibody bound on the oscillator (and thus in the solution) is related to the shift in vibrational frequency resulting from the addition of the specifically reactive substance.

N. Flowers et al., 1986, *Fed. Proc.*, vol. 45(6), page 1516, describes detecting a target single-stranded nucleic acid in a test solution by contacting the test solution with a surface of a piezoelectric oscillator, upon which a complementary single-stranded nucleic acid was immobilized, to allow hybridization of the complements. The amount of the target nucleic acid specifically bound on the oscillator (and thus in the test solution) is related to the shift in vibrational frequency resulting from the mass increase owing to the addition of the target nucleic acid.

SUMMARY OF THE INVENTION

In general, the invention features, in one aspect, a method for measuring or detecting a first member of a specific binding pair, the first member being capable of forming a complex with a second member of the specific binding pair, the method including immobilizing one of the members on a surface of a piezoelectric oscillator, determining a first vibrational frequency of the oscillator on which the member has been immobilized, contacting the surface of the oscillator on which the member has been immobilized with the other member under conditions permitting formation of the complex, and with a mass increasing particle (having a mass at least 1,000 times and more preferably 100,000 or 1,000,000 times greater than the first members) under conditions permitting binding of the particle with the complex, mass coupling the bound particle with the oscillator, and determining a second vibrational frequency of the oscillator with which the particle has been mass coupled, the difference between the first vibrational frequency and the second vibrational frequency being a measure of the quantity of the first member. As used herein, "mass coupling" of the mass-increasing particle means bringing the particle close enough to the oscillator surface such that, when the oscillator surface vibrates, the particle vibrates with it, rather than moving independently. Generally, the particle should be within 300, more preferably 200 or 100, angstroms of the oscillator surface to be effectively mass coupled to it.

In another aspect the invention features a method for detecting a first member of a specific binding pair in a sample, the first member being capable of forming a complex with a second member of the specific binding pair, the method including immobilizing one member on a surface of a piezoelectric oscillator, determining a first vibrational frequency of the oscillator on which the member has been immobilized, providing a particle binding member that includes a first binding region capable of binding to a binding site on the first member and a second binding region capable of binding to a binding site on a mass-increasing particle, contacting the surface of the oscillator on which the member has been immobilized with the sample under conditions permitting formation of the complex, with the particle binding member under conditions permitting binding of the particle binding member with the first member, and with the particle under conditions permitting binding of the particle with the particle binding member, mass coupling any bound particle with the oscillator, and determining a second vibrational frequency of the oscillator with which the particle has been mass coupled, the difference between the first vibrational frequency and the second vibrational frequency providing a measure of the quantity of the first member in the sample.

In preferred embodiments, the piezoelectric oscillator is an AT cut quartz crystal; the complex includes a nucleic acid hybrid, the second member includes a single stranded nucleic acid, and the first member includes a nucleic acid; the complex is an immunocomplex and the second member is an antibody or an antigen; the particle includes a polymer bead; the mass coupling includes drying the oscillator with which the particle has been bound; the particle includes a magnetic material (preferably iron oxide) and the mass coupling comprises applying a magnetic field to draw the particles toward the surface of the oscillator by magnetic attraction; the immobilizing includes coating the surface of the oscillator with a polymer, applying the second member onto the polymer coated surface, and grafting the second member to the polymer coated surface by UV irradiation; the binding site on the particle includes avidin adsorbed to the particle and the second binding region on the particle binding member includes biotin; the second binding region on the particle binding member is incapable of binding with the first member; the second binding region on the particle binding member includes a homopolymeric polynucleotide tail and the binding site on the particle includes a homopolymeric oligonucleoide complementary to the tail; the binding site on the particle includes a lectin; the particle has an effective diameter in the range 0.05 $\mu$ to 1.5 $\mu$; the mass coupling brings the particle within a distance of 250 $\mu$ from the surface of the oscillator; and the particle has a mass greater than 1000 times, more preferably greater than 100,000 or 1,000,000 times the mass of the first member.

Because the mass of each particle is relatively great in comparison to the masses of the binding pair members themselves, the mass coupling of the particles to the oscillator surface effectively amplifies the mass increase owing to the specific complexing of the detected binding pair member. As a result, the method of the invention provides an amplification of the frequency shift (and thus improved sensitivity) while providing a high specificity at low concentrations of the detected binding pair member in the sample. The method of the invention substantially extends the limits of sensitivity of piezoelectric detection systems.

Drawing the maqnetic particles to the oscillator surface by magnetic attraction allows mass coupling in solution, making it unnecessary to precede the vibrational frequency measurements with drying steps.

The method can be carried out quickly and easily using inexpensive and readily available materials.

Other features and advantages of the invention will be apparent from the following description of the preferred embodiments, and from the claims.

DESCRIPTION OF THE PREFERRED EMBODIMENTS

As an illustration of the invention, the following is a protocol by which the method of the invention can be used to screen a sample such as food or a clinical sample such as feces for the presence of contaminating Salmonella by detecting Salmonella DNA (corresponding to the first member of the specific binding pair) in the sample. The assay, in outline, operates as follows. First, a Salmonella-specific probe is immobilized on the surface of a piezoelectric oscillator. The target nucleic acid (DNA or RNA) of the sample is then contacted with the surface, under hybridizing conditions, so that hybrid complexes form between probe and sample DNA. In addition a mass-increasing particle (magnetic in the example below) is contacted with the surface under conditions which cause binding of the particle to the complex. For this purpose, in the example below, the particle bears a dT strand homologous with a poly A tail on an intermediate particle binding member having, in addition to the poly A tail, a nucleic acid sequence homologous with the target nucleic acid which allows the intermediate member to act as a bridge between the particle and the complex. A magnet is then used to mass couple the particle to the oscillator surface, thus amplifying the signal by significantly altering the vibrational frequency of the piezoelectric oscillator.

The first three steps described below were adapted from work of Newton Fawcett of the University of Tennessee.

1. Immobilizing the second member (probe) of the specific binding pair on the oscillator The Salmonella specific probe DNA is immobilized on the oscillator as follows. First, Salmonella-specific oliqonucleotide probes (e.g., 15-100, most preferably about 30, base pairs in length) are synthesized, by conventional methods. These probes contain sequences known to be Salmonella-specific; such specific sequences are known and described in the literature, e.g., in Fitts et al. (1983) J. Bacteriol, "Salmonella-Specific Sequences". The oscillator is coated with polymer and then the DNA probe is grafted to the polymer coated surface by UV irradiation according to techniques well known in the art. Specifically, one hundred parts of a solution of 0.1% poly(butylmethacrylate) in ethyl acetate is mixed with 1 part of a solution of 0.1% dimethoxyphenylacetophenone in acetone, and 10 $\mu$l of this mixture is evaporated onto the gold electrode pad of a 9 MHz AT-cut quartz crystal oscillator. The like electrode on the opposite side of the crystal is not treated with polymer. A 1 mg ml$^{-1}$ solution of probe DNA in 0.14 molar sodium phosphate buffer, pH 6.8, is applied to the polymer treated surface of the oscillator. Grafting of the DNA to the polymer is accomplished by irradiation with weak 365 nm (UV) light for 2 hours. Then an additional 10 $\mu$l of the DNA solution is applied to and grafted to the polymer treated surface by UV irradiation. Although the nature of the attaching bonds is unclear, such UV grafted DNA is sufficiently mobile to undergo subsequent hybridization yet sufficiently stably attached to resist removal during subsequent treatment steps. The probe-treated oscillator is washed as appropriate to remove any matter not stably attached.

2. Determining a first vibrational frequency of the oscillator

The oscillator with the DNA probe immobilized on it is then placed in a suitable oscillator circuit, and its vibrational frequency is measured, for example, using an electronic counter (Model 524C, Hewlett Packard, Palo Alto, CA) connected to a direct printout device (Beckman Printer, Model 1453, Beckman Instruments, Fullerton, CA), as will be familiar to one skilled in the art. Because the attachment of the DNA probe to the oscillator slightly increases the mass of the oscillator, this first vibrational frequency is slightly lower than the native frequency of the oscillator.

3. Contacting the probe treated oscillator with the sample

A food sample suspected of being contaminated with Salmonella is treated by well-known techniques to extract bacterial DNA (ribosome RNA could also be used), and then the DNA is denatured (for example by heating). A convenient known quantity of the denatured DNA, such as 10 $\mu$l of a 1 mg ml$^{-1}$ solution are then contacted with the probe-treated oscillator under conditions permitting hybridization of complementary base sequences of Salmonella DNA from the sample (i.e., target DNA) with probe DNA on the oscillator. For example, the probe-treated oscillator surface may be immersed in the solution of denatured sample DNA and allowed to incubate at 65° C. for 2 hours. The sample-treated oscillator is then washed as appropriate to remove any target DNA not hybridized with the attached probe DNA.

4. Binding mass-increasing particles to the hybridized target DNA

The hybridization of DNA from the sample with the oscillator fixed probe DNA again slightly increases the mass coupled with the oscillator, and thus causes a further slight decrease in the vibrational frequency of the oscillator below the measured first vibrational frequency.

According to the invention, this slight mass increase is greatly amplified by specifically associating comparatively massive particles with the target DNA hybridized with the probe DNA on the oscillator, and then mass coupling these specifically associated particles to the oscillator. This can be done directly or, as in this example, indirectly, through an intermediate bifunctional particle binding member interposed between the hybridized target DNA and the particle. The particle binding member contains a binding region that is capable of binding to a binding site on the hybridized target DNA, and another binding region that is capable of binding to a binding site on the particle. For example, the particle binding member can be composed of two nucleic acid regions, the first of which is a synthetic Salmonella-specific oligonucleotide (15–100, most preferably about 30, base pairs) different from probe oliqonucleotides (so a different region of target nucleic acid is bound), and the second of which is a homopolymeric tail, e.g., a conventional poly A tail. The particles (e.g., iron oxide microparticles such as are well-known) each bear a plurality of oligo dT's, complementary with the poly A tails, attached using conventional chemistry, e.g., glutaraldehyde coupling. The particle-binding member thus links the mass increasing particle to the oscillator surface only if target is present on that surface.

5. Mass coupling of the particles to the oscillator

After the particles have simply been attached to the oscillator surface, their effect on the vibrational frequency of the oscillator is not great because they are separated from the surface by a distance determined by the lengths of the coupling sequences; the particles thus by and large float in the surrounding medium, and move largely independently rather than vibrating with the oscillator surface.

According to the invention the effect of the particles is greatly amplified by mass coupling them to the oscillator surface, i.e., treating them to bring them within about 300, and more preferably 200 or 100, angstroms of the surface. In this illustration, the particles include a magnetic material and once they are associated with the hybridized target DNA they are coupled to the oscillator by applying a magnetic field to draw them toward the treated oscillator surface. Specifically, a magnet is positioned close to the oscillator wafer and behind it in relation to the treated oscillator surface, so that the particles are pulled toward the magnet and therefore close to the oscillator surface.

With the magnet so positioned and the particles so coupled, a second vibrational frequency measurement is made as described above, and the amplified frequency shift is determined. The quantity of target DNA hybridized to the immobilized probe DNA (and, thus, present in the sample) is then determined from this amplified frequency shift by making reference to a standard curve constructed from a series of test runs using samples containing known quantities of target DNA.

OTHER EMBODIMENTS

Other embodiments are within the following claims. For example, as will be apparent to one skilled in the art, members of specific binding pairs other than single-stranded nucleic acids may be detected by appropriate variation in detail from the protocol outlined above, without departing from the invention. For example, either or both members of the specific binding pair may be RNA, and antibody antigen pairs can also be used. Neither member of the pair need be a particularly massive entity, because the mass increase for effecting the measurable downshift in vibrational frequency is brought about by the particles and not by the binding pair members; the immobilized member must be capable of forming the specific complex with the member to be detected, and the member to be detected must be capable of forming the complex with the immobilized member and, in addition, must possess a binding site for binding, directly or indirectly, the particle.

As will be apparent to one skilled in the art, various modifications may be made in the protocol outlined in the illustration above without departing from the invention.

For example, in a particular application of the method the particles may be associated directly with the target, without the use of a particle binding member, simply by providing the particles with specific binding sites that bind directly to corresponding specific binding sites on the target.

In a particular application the steps of exposing the immobilized probe members to the sample, of exposing the complexed targets to the particles to permit direct or indirect association of the particles with the targets need not be performed in succession; instead any of these steps may be performed simultaneously, provided that the conditions required for the completion of the particular steps do not interfere with each other. Similarly, the targets may be bound to the particles prior to allowing the targets to complex with the probes, although this is less preferred because the mass and bulk of the particles may interfere with the capacity of the bound targets to form the complexes.

Rather than being composed entirely of magnetic material, the particles may contain magnetic material, as, for example, non magnetic polymer beads impregnated with a magnetic material rendering the particles magnetically active.

The particles need not contain magnetic material at all, but can rather be coupled to the oscillator by some alternative means, for example, by drying, as is customary in methods known in the art for piezoelectric mass sensing of biological binding pairs. The particles may be, for example, of a non-magnetic material such as depleted uranium.

The particle binding member, if one is employed, need not be a polynucleotide, but may instead be any bifunctional or polyfunctional entity having binding regions appropriate to the binding sites on the detected binding pair member and on the particle, respectively. For example, the particle may be specifically bound to the detected member by a biotin avidin linkage, by adsorbing the avidin to the particle and binding the biotin to the detected member by conventional means.

The second member of the binding pair may be immobilized on the oscillator surface by other means well-known in the coupling chemistry art; for example, the surface may be coated with any polymer having appropriate functional groups such as carboxylic acids, amines, thiols, or hydroxyls. Rather than immobilizing the probe and then contacting the oscillator with sample nucleic acid, the sample nucleic acid can be immobilized first and then contacted with probe.

We claim:

1. A method for measuring or detecting a first member of a specific binding pair, said first member being capable of forming a complex with a second member of said specific binding pair, said method comprising
   (a) immobilizing said first or second member on a surface of a piezoelectric oscillator,
   (b) determining a first vibrational frequency of said oscillator on which said member has been immobilized,
   (c) contacting said surface of said oscillator on which said member has been immobilized with (1) the other member under conditions permitting formation of said complex, and (2) a mass-increasing particle under conditions permitting binding of said particle with said complex,
   (d) mass coupling any said bound particle with said oscillator, and
   (e) determining a second vibrational frequency of said oscillator with which said particle has been mass coupled,
   the difference between said first vibrational frequency and said second vibrational frequency being a measure of the quantity of said first member.

2. A method for measuring or detecting a first member of a specific binding pair, said first member being capable of forming a complex with a second member of said specific binding pair, said method comprising
   (a) immobilizing a said member on a surface of a piezoelectric oscillator,
   (b) determining a first vibrational frequency of said oscillator on which said member has been immobilized,
   (c) providing a particle binding member comprising a first binding region capable of binding to a binding site on said first member and a second binding region capable of binding to a binding site on a mass-increasing particle,
   (d) contacting said surface of said oscillator on which said member has been immobilized with (1) said other member under conditions permitting formation of said complex, (2) said particle binding member under conditions permitting binding of said particle binding member with said first member, and (3) said mass-increasing particle under conditions permitting binding of said particle with said particle binding member,
   (e) mass coupling any said bound particle with said oscillator, and
   (f) determining a second vibrational frequency of said oscillator with which said particle has been mass coupled,
   the difference between said first vibrational frequency and said second vibrational frequency being a measure of the quantity of said first member in said sample.

3. A method for detecting a first member of a specific binding pair in a sample, said first member being capable of forming a complex with a second member of said specific binding pair, said method comprising
   immobilizing said second member on a surface of a piezoelectric oscillator,
   determining a first vibrational frequency of said oscillator on which said second member has been immobilized,
   contacting said surface of said oscillator on which said second member has been immobilized with said sample under conditions permitting formation of said complex,
   contacting said surface of said oscillator with which said sample has been contacted with a particle under conditions permitting binding of said particle with said first member,
   mass coupling any said bound particle with said oscillator, and
   determining a second vibrational frequency of said oscillator with which said particle has been mass coupled,
   the difference between said first vibrational frequency and said second vibrational frequency providing a measure of the quantity of said first member in said sample.

4. A method for detecting a first member of a specific binding pair in a sample, said first member being capable of forming a complex with a second member of said specific binding pair, said method comprising
   immobilizing said second member on a surface of a piezoelectric oscillator,
   determining a first vibrational frequency of said oscillator on which said second member has been immobilized,
   contacting said surface of said oscillator on which said second member has been immobilized with said sample under conditions permitting formation of said complex,
   providing a particle binding member comprising a first binding region capable of binding to a binding site on said first member and a second binding region capable of binding to a binding site on a particle,
   contacting said surface of said oscillator with which said sample has been contacted with said particle binding member under conditions permitting binding of said particle binding member with said first member,
   contacting said surface of said oscillator with which said particle binding member has been contacted with said particle under conditions permitting binding of said particle with said particle binding member,
   mass coupling any said bound particle with said oscillator, and
   determining a second vibrational frequency of said oscillator with which said particle has been mass coupled,
   the difference between said first vibrational frequency and said second vibrational frequency providing a measure of the quantity of said first member in said sample.

5. The method of claim 1 or 2 wherein said piezoelectric oscillator is an AT cut quartz crystal.

6. The method of claim 1 or 2 wherein said complex comprises a nucleic acid hybrid, said second member comprises a single stranded nucleic acid, and said first member comprises a nucleic acid.

7. The method of claim 1 or 2 wherein said complex is an immunocomplex and said second member is an antibody.

8. The method of claim 1 or 2 wherein said complex is an immunocomplex and said second member is an antigen.

9. The method of claim 1 or 2 wherein said particle comprises a polymer bead.

10. The method of claim 1 or 2 wherein said mass coupling comprises drying said oscillator with which said particle has been bound.

11. The method of claim 1 or 2 wherein said particle comprises a magnetic material and said mass coupling comprises applying a magnetic field to draw said particles toward said surface of said oscillator by magnetic attraction.

12. The method of claim 11 wherein said magnetic material comprises iron oxide.

13. The method of claim 5 wherein said immobilizing comprises coating said surface of said oscillator with a polymer, applying said second member onto said polymer coated surface, and grafting said second member to said polymer coated surface by UV irradiation.

14. The method of claim 2 wherein said binding site on said particle comprises avidin adsorbed to said particle and said second binding region on said particle binding member comprises biotin.

15. The method of claim 2 wherein said second binding region on said particle binding member is incapable of binding with said first member.

16. The method of claim 2 wherein said second binding region on said particle binding member comprises a homopolymeric polynucleotide tail and said binding site on said particle comprises a homooligomeric oligonucleotide complementary to said tail.

17. The method of claim 1 or 2 wherein said binding site on said particle comprises a lectin.

18. The method of claim 1 or 2 wherein said particle has an effective diameter in the range $0.05\ \mu$ to $1.5\ \mu$.

19. The method of claim 1 or 2 wherein said mass coupling brings said particle within a distance of $250\ \mu$ from said surface of said oscillator.

20. The method of claim 1 or 2 wherein said particle has a mass greater than 1,000 times the mass of said first member.

* * * * *